United States Patent
Amakawa

(10) Patent No.: US 7,915,452 B2
(45) Date of Patent: Mar. 29, 2011

(54) PROCESS FOR PRODUCING HIGHLY PURIFIED XYLTLENEDIAMINE

(75) Inventor: Kazuhiko Amakawa, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 633 days.

(21) Appl. No.: 11/630,648

(22) PCT Filed: Jun. 22, 2005

(86) PCT No.: PCT/JP2005/011431
§ 371 (c)(1), (2), (4) Date: Dec. 26, 2006

(87) PCT Pub. No.: WO2006/001298
PCT Pub. Date: Jan. 5, 2006

(65) Prior Publication Data
US 2009/0192334 A1    Jul. 30, 2009

(30) Foreign Application Priority Data
Jun. 23, 2004   (JP) .................................. 2004-184479

(51) Int. Cl.
*C07C 209/00* (2006.01)
(52) U.S. Cl. ....................................................... 564/385
(58) Field of Classification Search .................. None
See application file for complete search history.

(56) References Cited

U.S. PATENT DOCUMENTS

| | | | |
|---|---|---|---|
| 4,116,999 A | 9/1978 | Barchas | |
| 6,646,163 B2 * | 11/2003 | Nakamura et al. | 564/388 |
| 6,881,864 B2 * | 4/2005 | Amakawa et al. | 564/415 |
| 6,894,192 B2 * | 5/2005 | Amakawa | 564/415 |
| 2003/0013917 A1 | 1/2003 | Nakamura et al. | |

FOREIGN PATENT DOCUMENTS

| | | |
|---|---|---|
| EP | 1 193 244 A2 | 4/2002 |
| JP | 53-141238 | 12/1978 |
| JP | 2002-105035 | 4/2002 |
| JP | 2003-026638 | 1/2003 |
| JP | 2003-026639 | 1/2003 |
| WO | WO 2005/026103 A1 | 3/2005 |

OTHER PUBLICATIONS

JP2003-026639, machine translation.*
Supplementary European Search Report dated Apr. 18, 2008, for Application No. EP 05 75 3468.

* cited by examiner

*Primary Examiner* — Daniel M Sullivan
*Assistant Examiner* — Clinton Brooks
(74) *Attorney, Agent, or Firm* — Antonelli, Terry, Stout & Kraus, LLP.

(57) ABSTRACT

A method of producing xylylenediamine from xylene. In the method, xylene is converted into dicyanobenzene by ammoxidation. The produced dicyanobenzene is extracted into an organic solvent. The extract is then distilled to separate dicyanobenzene from the organic solvent. After added with a solvent, the separated dicyanobenzene is hydrogenated in a liquid phase. Finally, the hydrogenation product is purified by distillation to obtain a highly pure xylylenediamine. The method is conducted in a simple and low energy-consuming process.

4 Claims, 1 Drawing Sheet

PROCESS FOR PRODUCING HIGHLY PURIFIED XYLTLENEDIAMINE

TECHNICAL FIELD

The present invention relates to a method of producing xylylenediamine from xylylene, particularly, to a method of synthesizing a highly pure xylylenediamine by the catalytic hydrogenation of dicyanobenzene that is synthesized by the ammoxidation of xylene.

BACKGROUND ART

It is well known to produce xylylenediamine from xylene by the ammoxidation of xylene into dicyanobenzene and the subsequent hydrogenation of the resultant dicyanobenzene into xylylenediamine in the presence of a catalyst.

Non-Patent Document 1 discloses a method of producing xylylenediamine from xylene, in which xylene is ammoxidized into dicyanobenzene and the separated dicyanobenzene is hydrogenated into xylylenediamine in the presence of a catalyst. However, this document is quite silent about the details of the process such as the extraction of dicyanobenzene from the gas produced by the ammoxidation.

Patent Document 1 discloses a method of producing m-xylylenediamine from m-xylene. In the proposed method, isophthalonitrile produced by the ammoxidation of m-xylene is extracted into an organic solvent. Then, high-boiling point impurities are separated out in the first distillation step and the organic solvent is separated out in the second distillation step. Then, isophthalonitrile is taken out of the bottom of apparatus. The obtained purified isophthalonitrile is then hydrogenated after the addition of a specific solvent and liquid ammonia. This method requires increased costs for constructing production facilities because of its large number of steps. In addition, the method requires two distillation steps before the hydrogenation and further requires another distillation step for purification after the hydrogenation step. Therefore, a great quantity of energy for distillation should be consumed.

In the method disclosed in JP 2002-105035A, the ammoxidation gas containing dicyanobenzene from the ammoxidation of xylene is directly contacted with an organic solvent to extract dicyanobenzene into the organic solvent. The extracted dicyanobenzene is added with liquid ammonia and then hydrogenated without separation. Since the organic solvent for extracting dicyanobenzene from the ammoxidation gas should be stable under the hydrogenation conditions, the kind of organic solvent usable in this method is limited. Methylbenzonitrile, which is by-produced in the ammoxidation of xylene, is a suitable solvent for extracting dicyanobenzene from the ammoxidation gas because of its high dissolving power to dicyanobenzene. However, since the nitrile group of methylbenzonitrile is hydrogenated under the hydrogenation conditions, methylbenzonitrile cannot be effectively used as the solvent for extracting dicyanobenzene in the method of Patent Document 2 in which the solvent containing the extracted dicyanobenzene is directly fed into the hydrogenation step. Since methylbenzonitrile is an intermediate of the production of dicyanobenzene, methylbenzonitrile can be converted into dicyanobenzene if it can be recovered by separation and reused in the ammoxidation. However, the recovery of methylbenzonitrile is impossible in the proposed method for the reason mentioned above. In addition, xylylenediamine produced by this method usually contains a large amount of impurities, and therefore, may cause problems when used in applications requiring high purity, such as the production of high quality polyamide.

In the method of producing xylylenediamine disclosed in Patent Document 3, the ammoxidation gas from the ammoxidation of xylene is directly contacted with an organic solvent to extract dicyanobenzene in the ammoxidation gas into the organic solvent. The organic solvent containing the extracted dicyanobenzene is added with liquid ammonia and then dicyanobenzene is hydrogenated without separation. After the extraction using a specific solvent and water, xylylenediamine is finally purified by distillation. In this method, the kind of usable organic solvent is also limited because the organic solvent is required to be stable under the hydrogenation conditions. In addition, both the extraction and distillation are required to obtain a highly pure xylylenediamine, this making the process complicated and increasing the costs of constructing production facilities. Further, the distillation of the liquid mixture of xylylenediamine and water obtained by the water-extraction needs a great energy consumption, because a large amount of water having a large evaporation latent heat should be distilled away.

Patent Document 1: JP 2003-26639A
Patent Document 2: JP 2002-105035A
Patent Document 3: JP 2003-26638A
Non-Patent Document 1: Process Handbook (1978) edited by The Japan Petroleum Institute

DISCLOSURE OF THE INVENTION

As mentioned above, the conventional methods for producing a highly pure xylylenediamine require a complicated and a large energy-consuming process, for example, the steps of purification by distillation before and after the hydrogenation (method of Patent Document 1) and the step of purification by both extraction and distillation (method of Patent Document 3). Thus, the present invention is directed to provide a method of producing a highly pure xylylenediamine by a simple and low energy-consuming process, in which xylene is ammoxidized into dicyanobenzene, which is then hydrogenated into xylylenediamine.

As a result of extensive research in view of attaining the above object, it has been found that a highly pure xylylenediamine is produced by a method which includes the steps of extracting dicyanobenzene in an ammoxidation gas into an organic solvent, separating the resultant organic solution into the organic solvent and dicyanobenzene by distillation, hydrogenating the separated dicyanobenzene in a liquid phase after adding a solvent, and purifying the hydrogenation product by distillation.

Thus, the present invention provides a method of producing xylylenediamine from xylene, which includes:

(1) an ammoxidation step in which xylene is allowed to react with ammonia and oxygen in a vapor phase in the presence of a catalyst, thereby obtaining an ammoxidation gas containing dicyanobenzene;

(2) an extraction step in which the ammoxidation gas is bought into contact with an organic solvent having a boiling point lower than that of dicyanobenzene, thereby extracting dicyanobenzene into the organic solvent to obtain a dicyanobenzene-containing solution;

(3) a distillation step in which the dicyanobenzene-containing solution from the extraction step is distilled to be separated into the organic solvent and dicyanobenzene;

(4) a hydrogenation step in which, after adding a reaction solvent, the separated dicyanobenzene from the distillation step is hydrogenated in a liquid phase in the presence of a catalyst to obtain a solution containing xylylenediamine; and (5) a purification step in which the solution containing xylylenediamine from the hydrogenation step is distilled to obtain a highly pure xylylenediamine.

BEST MODE FOR CARRYING OUT THE INVENTION

Figure 1:
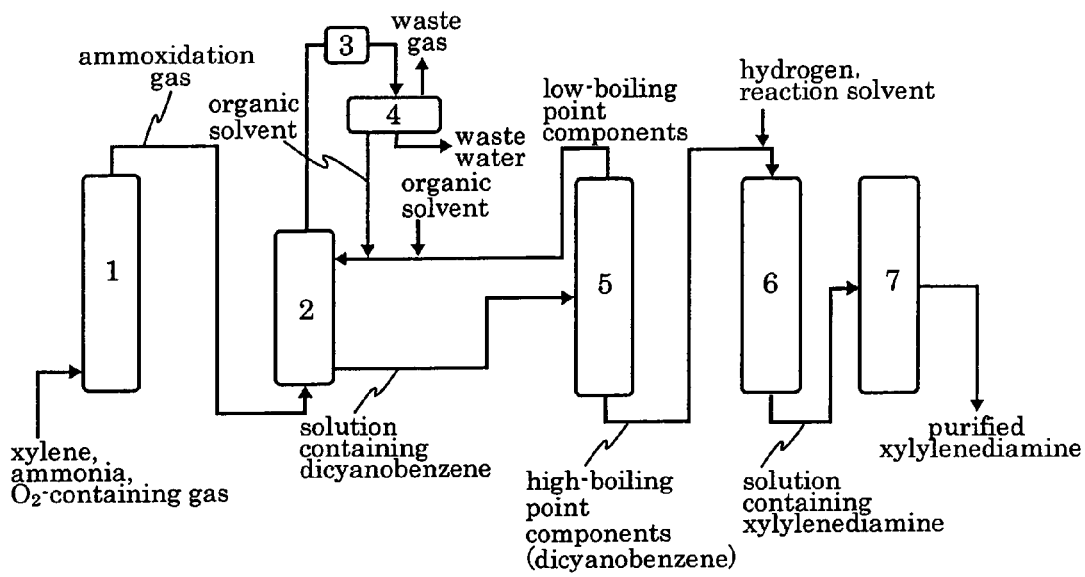
FIG. 1 is a flow diagram illustrating one embodiment of the production method of xylylenediamine of the invention.

The raw material used in the production method of the invention is xylene, with m-xylene and p-xylene being preferred, and m-xylene being most preferred. The xylene isomers may be used alone or in combination of two or more. By the ammoxidation, m-xylene and p-xylene are converted correspondingly into isophthalonitrile and terephthalonitrile, these dicyanobenzenes being converted corresponding into m-xylylenediamine and p-xylylenediamine by the subsequent hydrogenation.

(1) Ammoxidation Step

In the ammoxidation step, xylene is allowed to react with ammonia and oxygen in a vapor phase in the presence of a catalyst, thereby being converted into dicyanobenzene such as isophthalonitrile and terephthalonitrile. The ammoxidation is carried out by any of known methods without specific limitation. In a typical method, dicyanobenzene is produced under the conditions of 300 to 500° C., atmospheric pressure to 0.3 MPaG and 0.1 to 30 s contact time while introducing a gas containing xylene, ammonia and oxygen into a reactor in which a solid catalyst is placed. Preferably, 2 to 20 by volume of ammonia and 2 to 20 by volume of oxygen are used per one volume of xylene. The preferred catalyst contains at least one oxide selected from the group consisting of oxides of metals such as vanadium, molybdenum and iron, with a catalyst containing vanadium being preferred. Examples of the catalysts include V—Cr—B—Mo-containing catalysts (JP 11-209332A) and Fe—Sb—V-containing catalysts (JP 9-71561A). The contact time (reciprocal of space velocity) of the raw material gas is from 0.1 to 30 s, preferably from 0.1 to 15 s, and particularly preferably from 0.2 to 8 s on the basis of the volume at the reaction temperature and reaction pressure. The ammoxidation is conducted in any of fixed bed manner, fluidized bed manner and moving bed manner. Air is preferably used as the source of oxygen.

(2) Extraction Step

The ammoxidation gas containing dicyanobenzene from the ammoxidation step is introduced into the extraction step where the ammoxidation gas is brought into contact with an organic solvent, to extract dicyanobenzene into the organic solvent. Organic solvents having a boiling point lower than that of dicyanobenzene are used. It is preferred that the organic solvent has a high dicyanobenzene solubility and is inert to dicyanobenzene. The organic solvent is preferably selected from the group consisting of alkylbenzenes and benzonitriles, with benzonitriles being particularly preferred. Examples of alkylbenzenes include toluene, m-xylene, p-xylene, pseudocumene, mesitylene and ethylbenzene, and examples of benzonitriles include benzonitrile, methylbenzonitrile and dimethylbenzonitrile. These organic solvents may be used alone or in combination of tow or more. Since methylbenzonitrile is a by-product of the ammoxidation, the kind of chemical species included in the process can be reduced by the use thereof as the organic solvent. In addition, since it is a good solvent for dicyanobenzene, methylbenzonitrile is particularly preferred as the organic solvent.

The contact of the ammoxidation gas and the organic solvent may be carried out, but not limited to, by blowing the ammoxidation gas directly into a container filled with the organic solvent, or by spraying the organic solvent into the ammoxidation gas. By the contact of the ammoxidation gas and the organic solvent, dicyanobenzene and methylbenzonitrile by-produced in the ammoxidation are extracted by the dissolution into the organic solvent, thereby being separated from gases such as non-reacted ammonia, hydrogen cyanide, carbon dioxide, water, carbon monoxide, nitrogen and oxygen. The contact conditions depend upon the kind of organic solvent used and the manner for performing the extraction step. Generally, the pressure is selected from a range from atmospheric pressure to the reaction pressure of the ammoxidation. The temperature is selected so that the resultant dicyanobenzene-containing solution is kept within a range from 50 to 200° C. The organic solvent is used from 1 to 30 times the weight of dicyanobenzene. When methylbenzonitrile is used as the organic solvent, the temperature of the dicyanobenzene-containing solution is preferably from 100 to 200° C. and the organic solvent is used preferably from 1 to 10 times the weight of dicyanobenzene. The dicyanobenzene-containing solution thus obtained is introduced into the distillation step.

(3) Distillation Step

In the distillation step, the dicyanobenzene-containing solution from the extraction step is distilled to separate the organic solvent and dicyanobenzene by recovering the organic solvent from the top of column and taking out dicyanobenzene from the bottom of column. The high-boiling point components are separated together with dicyanobenzene without being removed. The separated dicyanobenzene is introduced into the hydrogenation step. At least a part of the organic solvent recovered from the top of column is preferably reused in the extraction step. It is preferred in the invention to separate methylbenzonitrile by-produced in the ammoxidation by recovering it from the top of column together with the organic solvent. The separated methylbenzonitrile may be used as a part of the organic solvent in the extraction step. Alternatively, after separated from the organic solvent by distillation, methylbenzonitrile may be recycled into the ammoxidation step where it is converted into dicyanobenzene. In particular, when methylbenzonitrile is used as the organic solvent in the extraction step, the organic solvent recovered from the top of distillation column is mainly composed of methylbenzonitrile. Namely, the methylbenzonitrile used as the organic solvent and the methylbenzonitrile by-produced in the ammoxidation are recovered simultaneously. By recycling the methylbenzonitrile which is by-produced in the ammoxidation to the ammoxidation, the yield of dicyanobenzene based on the starting xylene can be increased, this in turn resulting in the increase of xylylenediamine. Thus, the method of the invention is advantageous because the by-produced methylbenzonitrile is effectively reused.

Since dicyanobenzene is thermally instable and easily degraded, particularly in the presence of high-boiling point by-products of ammoxidation and the ammoxidation catalyst, the distillation is conducted preferably at temperatures as low as possible and preferably under reduced pressure. The distillation column is operated preferably under from 2 to 30 kPa and still more preferably under from 3 to 20 kPa so as to prevent dicyanobenzene from precipitating in the distillation column. In the distillation of high-melting point compound, the clogging due to the precipitation of crystals can be generally prevented by operating the distillation column at temperatures higher than the melting point of high-melting point compound. However, if a solvent is present in the distillation column in an amount enough to dissolve the high-melting point compound, the precipitation of crystals does not occur even when the distillation column is operated at temperatures lower than the melting point of high-melting point compound. The distribution of the dicyanobenzene concentration throughout the distillation column depends on the chemical composition of liquid being supplied, the position from which the liquid is supplied, the separation conditions of distillate and bottom product, and the vapor-liquid equilibrium. The distribution of temperature changes according to the operating pressure. The solubility of dicyanobenzene to the organic solvent is determined uniformly by the temperature. Therefore, the precipitation of dicyanobenzene in the distillation column is governed mainly by the operating pressure. For example, in the distillation of isophthalonitrile in 3-methylbenzonitrile as the extracting organic solvent, a region where the temperature is lower than the melting point of isophthalonitrile and the concentration of isophthalonitrile is higher than its solubility to 3-methylbenzonitrile is generated when the distillation column is operated under 4.2 kPa or lower. In such region, isophthalonitrile precipitates to clog the distillation column. Therefore, the distillation column is operated under high vacuum conditions within the range so as not to cause the precipitation of dicyanobenzene in the distillation column. For example, the raw material is xylene, dicyanobenzene is isophthalonitrile and the organic solvent is 3-methylbenzonitrile, the pressure of distillation column is preferably from 5 to 10 kPa.

The temperature of the column bottom during distillation is preferably from 160 to 235° C., and more preferably from 170 to 225° C. In particular, the temperature of the bottom liquid is preferably from 165 to 200° C. when dicyanobenzene is isophthalonitrile or a mixture of isophthalonitrile and terephthanonitrile. Within the above range, the degradation and solidification of dicyanobenzene can be prevented. The degradation of dicyanobenzene decreased not only the yield of xylylenediamine but also the purity of xylylenediamine in some cases if the degraded dicyanobenzene is included in dicyanobenzene which is supplied to the hydrogenation step. To obtain a high-purity xylylenediamine, it is important to suitably control the temperature of the column bottom. Dicyanobenzene taken out of the bottom of distillation column usually contains a small amount of high-boiling point impurities.

(4) Hydrogenation Step

The liquid dicyanobenzene taken out of the bottom of distillation column is transferred into the hydrogenation step, where dicyanobenzene is hydrogenated after added with a solvent for hydrogenation. In the method of the invention, the hydrogenation is conducted in a liquid phase using the reaction solvent. Various solvents that are stable under the hydrogenation conditions can be used as the reaction solvent. Examples thereof include hydrocarbon solvents such as toluene, xylene and trimethylbenzene; ether solvents such as tetrahydrofuran and dioxane; lower aliphatic amide solvents such as dimethylformamide and dimethylacetamide; alcohol solvents such as methanol, ethanol and propanol; and ammonia. These solvents may be used alone or in combination of two or more. By the use of ammonia, the yield of xylylenediamine is increased. Therefore, it is preferred to use ammonia as a part of, more preferably 5 to 100% by weight of the reaction solvent. The hydrogenation solvent is used preferably in an amount of 1 to 99 parts by weight, more preferably 1.5 to 99 parts by weight per one part by weight of dicyanobenzene.

A hydrogen-containing gas to be used for the hydrogenation of dicyanobenzene may contain impurities, which are inert to the hydrogenation, such as methane and nitrogen. However, a high total pressure is needed to attain a sufficient hydrogen partial pressure if the content of impurities is excessively high, to make the process industrially disadvantageous. Therefore, the hydrogen concentration of the hydrogen-containing gas is preferably 50 mol % or more.

The hydrogenation catalyst may be selected from known supported or non-supported metal catalysts, Raney catalysts, etc., with catalysts containing, as the active metal component, at least one metal selected from the group consisting of nickel, cobalt, palladium, ruthenium and rhodium being preferred, catalysts containing nickel and/or cobalt being more preferred, and catalysts containing nickel being still particularly preferred. The carrier for the supported catalyst may be alumina, silica, titania, zirconia, etc. The catalyst for hydrogenation may be modified, if necessary, by adding at least one metal selected from the group consisting of Li, Na, K, Rb, Cs, Be, Ca, Ba, Ti, Cu, Cr, Zn, Mn, Mg, Fe, Ga, Ge, Nb, Ir, Pt, Bi, Al, Si, In, Sr, Ce, and Mo.

The hydrogenation may be carried out in the presence of an optional additive for promoting the reaction and increasing the yield. Examples of the additives include hydroxides and alcoholates of alkali metals or alkaline earth metals, such as lithium hydroxide, sodium hydroxide and potassium hydroxide.

The hydrogenation may be conducted in either of fixed bed or slurry bed manner and in either of batchwise or continuous manner, with a fixed bed, continuous flow manner being preferred because of its easiness to perform. The hydrogenation temperature is preferably from 20 to 250° C., and more preferably from 20 to 200° C. The hydrogenation pressure is preferably from 0.5 to 30 MPaG, and more preferably from 1 to 20 MPaG when expressed by the hydrogen partial pressure. The amount of the catalyst to be used is preferably from 0.1 to 200 parts by weight per 100 parts by weight of the starting dicyanobenzene for the batchwise hydrogenation. In the continuous hydrogenation, it is preferred to supply the starting dicyanobenzene at a rate of 0.01 to 1000 parts by weight/h per 100 parts by weight of the catalyst.

In view of the production efficiency of xylylenediamine, it is preferred to select the hydrogenation conditions such as the reaction temperature and the supplied amount of dicyanobenzene so that the conversion of dicyanobenzene reaches substantially 100 mol % and the yield of cyanobenzylamine (hydrogenation intermediate, 3-cyanobenzylamine if the raw material is isopythalonitrile) is made as low as possible. The cyanobenzylamine intermediate is difficult to be separated from the corresponding xylylenediamine by usual distillation, because the difference between the boiling points is small. Therefore, to produce xylylenediamine in a high purity, it is preferred to control the concentration of cyanobenzylamine low at the outlet of hydrogenation. By conducting the hydrogenation under the conditions mentioned above, the purification of xylylenediamine becomes easy.

(5) Purification Step

The solution containing xylylenediamine from the hydrogenation step is transferred into the purification step where xylylenediamine is purified by distillation. By the distillation, the solvent, low-boiling point by-products and high-boiling point by-products are separated from the solution to obtain a highly pure xylylenediamine. The distillation is performed in either batchwise or continuous manner using a known distillation apparatus such as a packed column, a plate column and a flash dram. The solvent is separated by distillation under a pressure which is determined depending upon the boiling point of the solvent. The boiling point of the solvent is generally lower than that of xylenediamine. When ammonia is used as the hydrogenation solvent, it is preferred to first separate ammonia from the hydrogenation product solution by distillation under pressure, and then, purify xylylenediamine by distillation under reduced pressure. The recovery of ammonia by distillation is preferably conducted at 70 to 200° C. under pressure of 0.2 to 3 MPa. In the distillation of the solvent other than ammonia, low-boiling point by-products and high-boiling point by-products, the pressure is preferably 1 to 30 kPa and particularly preferably 1 to 10 kPa, and the bottom temperature of the distillation apparatus is preferably 80 to 195° C. and particularly preferably 100 to 185° C. If the product solution from the hydrogenation contains a considerable amount of cyanobenzylamine, an additional treatment for removing cyanobenzylamine such as a treatment by an alkali agent (JP 45-14777B) and a treatment by an iron-containing catalyst (JP 57-27098A) may be combinedly employed.

In the method of the invention, a highly pure xylylenediamine having a purity of 99.9% or more is produced by the steps mentioned above. As compared with the known methods of producing xylylenediamine proposed, for example, in Patent Documents 1 and 3, the method of the invention is simple and low energy-consuming. The highly pure xylylenediamine produced by the method of the invention is particularly suitable as the raw material for the production of polyamide resins having an excellent quality.

The method of the invention will be explained in more detail with reference to the attached drawings. FIG. 1 is a flow diagram illustrating one embodiment of the invention. It should be noted that the invention is not limited thereto. In FIG. 1, the ammoxidation gas from an ammoxidation reactor 1 is introduced into an extraction column 2 having an extraction zone composed of plates or packed bed. The organic solvent for extraction is fed from the upper portion of the extraction column. By the contact with the organic solvent, dicyanobenzene and by-produced methylbenzonitrile in the ammoxidation gas enter into the organic solvent. The gases not extracted into the organic solvent, such as ammonia, hydrogen cyanide, carbon dioxide, water, carbon monoxide, nitrogen and oxygen, are exhausted through the top portion of the extraction column together with vapor of the organic solvent. The gas from the outlet of the extraction column is cooled by a condenser 3 where the condensable components such as the organic solvent and water are condensed, and then, introduced into a separator 4 to be separated into the organic solvent, waste water and waste gas. The separated organic solvent is returned to the extraction column 2 for reuse. The waste water and waste gas are transferred into a waste disposer. The dicyanobenzene-containing solution from the extraction column 2 is fed into a distillation column 5, to be separated into a low-boiling point component such as the organic solvent and a high-boiling point component such as dicyanobenzene. The organic solvent recovered from the top of the distillation column is returned into the extraction column 2 for reuse. The dicyanobenzene recovered from the bottom of the distillation column is added with a reaction solvent for hydrogenation and hydrogen, and introduced into a hydrogenation reactor 6 where dicyanobenzene is hydrogenated into xylylenediamine. The solution containing xylylenediamine from the outlet of the hydrogenation reactor is fed into a purification apparatus 7 to obtain the highly pure xylylenediamine. The purification apparatus 7 is composed of three distillation columns: a distillation column for separating ammonia, a distillation column for separating low-boiling point component, and a distillation column for separating high-boiling point component.

EXAMPLES

The present invention will be described in more detail by reference to the examples. However, it should be noted that the following examples are only illustrative and the scope of the invention is not limited thereto. In the following examples, the chemical compositions were determined by gas chromatographic analysis.

Example 1

In accordance with the process flow shown in FIG. 1, the ammoxidation, the extraction of dicyanobenzene, the distillation of extract, the hydrogenation and the purification of xylylenediamine were conducted. From the obtained xylylenediamine, a polyamide resin was produced and then made into a film.

(1) Ammoxidation Step

A silica-supported catalyst for fluidized bed ammoxidation was prepared according to the method described in JP 6-23158B. The content of silica was 50% by weight and the other components were composed of V, Cr, Mo and B in a ratio of 1:1:0.1:0.2. Into a fluidized bed ammoxidation reactor 1, was packed 6 kg of the catalyst. The ammoxidation was conducted while supplying a raw material gas composed of 3% of m-xylene, 21% of ammonia and 76% of air, each based on volume, under the conditions of a reaction temperature of 400° C., a space velocity of 700 $h^{-1}$, and a pressure of 0.05 MPaG. The yields were 80.2 mol % for isophthalonitrile and 3.7 mol % for 3-methylbenzonitrile, each based on m-xylene fed into the reaction system.

(2) Extraction Step

The ammoxidation gas from the ammoxidation reactor 1 was introduced into the extraction column 2 from its bottom portion. The extraction column 2 was a tower-shaped vessel made of SUS 304. The inner diameter of the cylindrical body portion was 100 mm and the height was 800 mm. At its bottom portion, an inlet for the ammoxidation gas and an outlet for the dicyanobenzene-containing solution were provided. At its vertically central portion, a dumped packing made of metal was packed. From the upper portion of the extraction column, 3-methylbenzonitrile (solvent for extraction) was supplied at a rate of 1 kg/h, to bring the ammoxidation gas into continuous contact with the solvent. The temperature of the liquid at its bottom portion was kept at 160° C. The chemical composition of the solution taken out of the bottom was 24.9% by weight of isophthalonitrile, 74.5% by weight of 3-methylbenzonitrile and 0.6% by weight of other high-boiling point components.

(3) Distillation Step

The extract from the extraction column was introduced into the distillation column 5 for distilling the extract from its middle portion. The distillation was conducted continuously at a column top temperature of 120° C. and a column bottom temperature of 180° C. under reduced pressure of 6 kPa.

(4) Hydrogenation Step

Into isophthalonitrile recovered from the bottom of the distillation column, a hydrogenation solvent (mixture of m-xylene and liquid ammonia) were added to prepare a hydrogenation raw material, the chemical composition of which was isophthalonitrile/m-xylene/ammonia=Jun. 10, 1984 by weight.

Into the 4-L fixed bed hydrogenation reactor 6, was packed 5 kg of a Ni/diatomaceous earth catalyst (Ni content: 50% by weight). The hydrogenation raw material was supplied into the reactor from its upper portion at a rate of 5.6 kg/h. The hydrogenation was conducted at 90° C. under 12 MPa while flowing hydrogen (purity: 99% or more) in parallel from the upper portion of the reactor. The yield of m-xylylenediamine of the hydrogenation was 93% based on isophthalonitrile.

(5) Purification Step

The solution containing m-xylylenediamine was fed into the purification apparatus 7 where the hydrogenation product solution was distilled to be separated into low-boiling point components (ammonia, m-xylene, methylbenzylamine by-produced in the hydrogenation, etc.) and high-boiling point components. The hydrogenation product solution was first distilled in a distillation column for separating ammonia under 0.5 MPa at a bottom temperature of 150° C. to separate out ammonia. The remaining bottom liquid was then distilled in a distillation column for separating low-boiling point components under 6 kPa at a bottom temperature of 182° C. to separate out the low-boiling point components such as m-xylylene and methylbenzylamine. The obtained bottom liquid was then distilled in a distillation column for separating high-boiling point components under 2.6 kPa at a bottom temperature of 173° C. to separate out the high-boiling point components, thereby recovering the purified m-xylylenediamine from the top of the column. The chemical composition of the purified product was 99.98% by weight of m-xylylenediamine, 0.01% by weight of 3-methylbenzylamine and 0.01% by weight of other components.

(6) Production of Polyamide Resin

A polyamide resin was produced from m-xylylenediamine obtained above, which was then continuously extruded into a non-stretched film. The polyamide resin was evaluated by the following methods.

(i) Relative Viscosity of Polyamide Resin

Accurately weighed one gram of polyamide resin was dissolved in 100 cc of 96% sulfuric acid at 20 to 30° C. under stirring. Immediately after complete dissolution, 5 cc of the resulting solution was placed in a Canon Fenske viscometer, and the viscometer was allowed to stand in a thermostatic chamber maintained at 25±0.03° C. for 10 min. Then, a dropping time (t) of the solution was measured. Also, a dropping time ($t_0$) of the 96% sulfuric acid was measured. The relative viscosity was calculated from the measured t and $t_0$ according to the following formula:

Relative Viscosity=$t/t_0$.

(ii) Yellowness Index (YI) of Non-Stretched Film

The tristimulus values X, Y and Z of XYZ colorimetric system of reflected light were measured according to JIS-K7103 using a color difference meter Σ80 model available from Nippon Denshoku Co., Ltd., and the yellowness index (YI) was calculated from the following formula:

$YI=100\times(1.28X-1.06Z)/Y$.

To a molten adipic acid heated to 180° C. in a reactor equipped with a stirrer and a partial condenser, m-xylylenediamine obtained above was added dropwise under atmospheric pressure while raising the temperature. The dropwise addition of m-xylylenediamine was stopped when the inner temperature reached 250° C. After reaching 255° C., the pressure was kept at 60 kPa and the temperature was raised to 260° C. over 20 min. Thereafter, the reaction product was taken out, cooled, and granulated, to obtain poly(m-xylylene adipamide) (nylon MXD6) having a molar balance of 0.995 and a relative viscosity of 2.20. The molar balance is a molar ratio of the units derived from diamine monomer and the units derived from dicarboxylic acid monomer (diamine unit/dicarboxylic acid unit) each constituting the polyamide backbone inclusive of terminal ends.

(7) Continuous Extrusion of Polyamide Resin

After vacuum-drying at 120° C. for 6 h, the polyamide resin was extruded into a non-stretched film of 150 μm thick at 260° C. from an extruder having a screw of 40 mm diameter. The extrusion into a 150 μm thick non-stretched film was continued for five days. During the continuous extrusion, serious problems which prevented the continuous operation, such as burning of die and the dirt of cooling roll, did not occur. During the continuous extrusion, the non-stretched film was sampled every 8 h to measure the yellowness index. Each sampled non-stretched film was fixed onto a flame and then kept in a thermostatic chamber at 150° C. for one hour for crystallization and heat treatment. Thereafter, the yellowness index (YI) of reflected light was measured. The measured YI values fell within a range from 5.8 to 6.4, indicating the stable quality of non-stretched films.

Example 2

In the same manner as in Example 1, each step of ammoxidation, extraction, distillation, hydrogenation and purification was conducted except for using a mixed xylene (80% by weight of m-xylene and 20% by weight of p-xylene) as the raw material. The yield of dicyanobenzene (total of meta and para isomers, the same applied below) in the ammoxidation was 80.9 mol %. The chemical composition of the dicyanobenzene-containing solution taken out of the bottom of the extraction column was 24.9% by weight of dicyanobenzene, 74.5% by weight of 3-methylbenzonitrile and 4-methylbenzonitrile in total, and 0.6% by weight of other high-boiling point components. In the distillation step, the column top temperature was 120° C. and the column bottom temperature was 182° C. The yield of xylylenediamine (total of meta and para isomers, the same applied below) in the hydrogenation step was 92% based on dicyanobenzene. The chemical composition of purified product obtained in the purification step was 99.98% by weight of xylylenediamine, 0.01% by weight of 3-methylbenzylamine and 4-methylbenzylamine in total, and 0.01% by weight of other components.

Comparative Example 1

Figure 2:
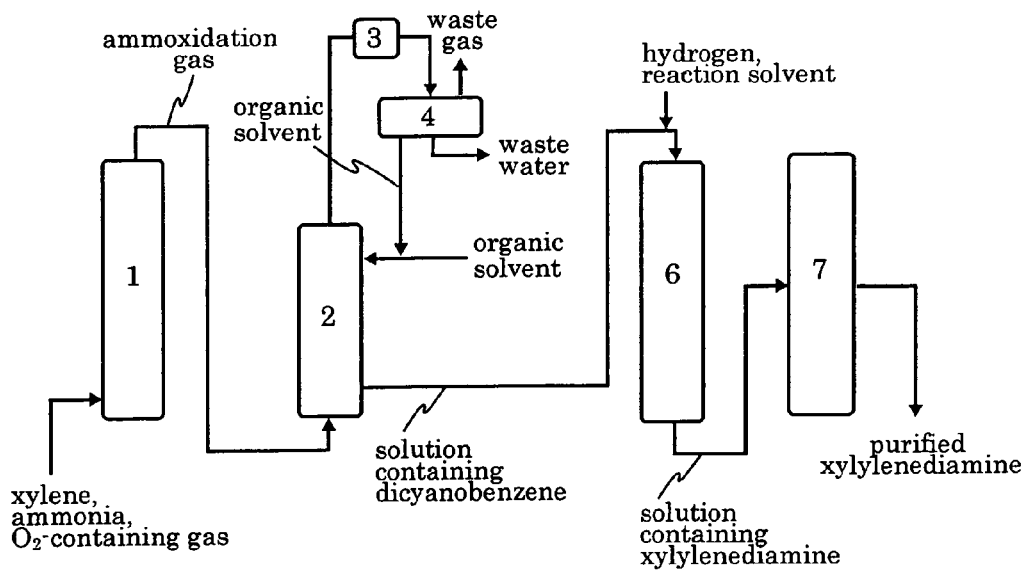
FIG. 2 is a flow diagram illustrating the production method of xylylenediamine disclosed in Patent Document 2.

Each step of the ammoxidation, extraction of dicyanobenzene, hydrogenation and purification of xylylenediamine was conducted in accordance with the method of Patent Document 2 shown in FIG. 2, in which like reference numerals indicate like parts as in FIG. 1. Using xylylenediamine obtained, a polyamide resin was produced, which was then made into a film.

(1) Ammoxidation Step

A silica-supported catalyst for fluidized bed ammoxidation was prepared according to the method described in JP 6-23158B. The content of silica was 50% by weight and the other components were composed of V, Cr, Mo and B in a ratio of 1:1:0.1:0.2. Into a fluidized bed ammoxidation reactor 1, was packed 6 kg of the catalyst. The ammoxidation was conducted while supplying a raw material gas composed of 3% of m-xylene, 21% of ammonia and 76% of air, each based on volume, under the conditions of a reaction temperature of 400° C., a space velocity of 700 $h^{-1}$, and a pressure of 0.05 MPaG. The yields were 80.2 mol % for isophthalonitrile and 3.7 mol % for 3-methylbenzonitrile, each based on m-xylene fed into the reaction system.

(2) Extraction Step

The ammoxidation gas from the ammoxidation reactor was introduced into an extraction column 2 from its bottom portion. The extraction column was a tower-shaped vessel made of SUS 304. The inner diameter of the cylindrical body portion was 100 mm and the height was 800 mm. At its bottom portion, an inlet for the ammoxidation gas and an outlet for the extract were provided. At its vertically central portion, a dumped packing made of metal was packed. From the upper portion of the extraction column, pseudocumene (solvent for extraction) was supplied at a rate of 1 kg/h, to bring the ammoxidation gas into continuous contact with the solvent. The temperature of the liquid at the bottom portion was kept at 145° C. The chemical composition of the solution taken out of the bottom was 24.9% by weight of isophthalonitrile, 73.3% by weight of pseudocumene, 1.1% by weight of 3-methylbenzonitrile and 0.7% by weight of other high-boiling point components.

(3) Hydrogenation Step

Into the extract, 3.1 times by weight of liquid ammonia was added to prepare a hydrogenation raw material. Into a 4-L fixed bed hydrogenation reactor 6, was packed 5 kg of a Ni/diatomaceous earth catalyst (Ni content: 50% by weight). The hydrogenation raw material was supplied into the reactor from its upper portion at a rate of 5.6 kg/h. The hydrogenation was conducted at 90° C. under 12 MPa while flowing hydrogen in parallel from the upper portion of the reactor. The yield of m-xylylenediamine in the hydrogenation was 92% based on isophthalonitrile. During the hydrogenation, 3-methylbenzonitrile in the hydrogenation raw material disappeared, and instead, the formation of a considerable amount of 3-methylbenzylamine which might be derived from 3-methylbenzonitrile was found.

(4) Purification Step

The hydrogenation product solution was fed into a purification apparatus 7 for purifying xylylenediamine with the same construction and the same performance as used in the examples, where the solution was distilled to be separated into low-boiling point components (ammonia, pseudocumene, methylbenzylamine by-produced in the hydrogenation, etc.) and high-boiling point components. The chemical composition of the purified product was 99.81% by weight of m-xylylenediamine, 0.01% by weight of 3-methylbenzylamine, 0.15% by weight of dimethylbenzyl alcohol and 0.03% by weight of other components.

(5) Production of Polyamide Resin

In the same manner as in Example 1 except for using m-xylylenediamine obtained above, poly(m-xylylene adipamide) (nylon MXD6) having a molar balance of 0.996 and a relative viscosity of 2.22 was produced.

(6) Continuous Extrusion of Polyamide Resin

After vacuum-drying at 120° C. for 6 h, the polyamide resin was extruded into a non-stretched film of 150 μm thick at 260° C. from an extruder having a screw of 40 mm diameter. The extrusion into a 150 μm thick non-stretched film was continued for five days. During the continuous extrusion, the adhesion of tarry substance to the die was found, which tarry substance frequently adhered also to the non-stretched film. In addition, the cooling roll was soiled. Therefore, the extrusion was discontinued three times for cleaning during the continuous operation. During the continuous extrusion, the non-stretched film was sampled every 8 h to measure the yellowness index in the same manner as in Example 1. The measured YI values varied widely from 6.2 to 8.7.

Xylylenediamine produced by the method of Comparative Example 1 contained a large amount of impurities. In addition, methylbenzonitrile by-produced in the ammoxidation disappeared in the hydrogenation step. Therefore, methylbenzonitrile could not be effectively reused, for example, for converting into dicyanobenzene by recycling to the ammoxidation step. In addition, the polyamide resin produced from such xylylenediamine was inferior to the polyamide resin of Example 1 in the stability of continuous film formation and quality of film being produced.

INDUSTRIAL APPLICABILITY

By the method of the invention, a highly pure xylylenediamine (purity: 99.9% by weight or more) is produced in a simple and low energy-consuming process. By using the highly pure xylylenediamine produced according to the invention, a polyamide resin of a high quality excellent in the stability during the molding process and excellent in color tone is produced. In addition, methylbenzonitrile by-produced in the ammoxidation can be effectively used in the method of the invention. Thus, the present invention is industrially greatly advantageous. Xylylenediamine produced according to the invention is industrially useful as raw materials for polyamide resins, epoxy curing agents, etc. and intermediate materials for isocyanates.

The invention claimed is:

1. A method of producing xylylenediamine from xylene, which consists of:
    (1) an ammoxidation step in which xylene is allowed to react with ammonia and oxygen in a vapor phase in the presence of a V—Cr—B—Mo-containing-catalyst, thereby obtaining an ammoxidation gas containing dicyanobenzene;
    (2) an extraction step in which the ammoxidation gas is bought into contact with an organic solvent comprising methylbenzonitrile, thereby extracting dicyanobenzene into the organic solvent to obtain a dicyanobenzene-containing solution;
    (3) a distillation step, in a distillation column, in which the dicyanobenzene-containing solution from the extraction step is distilled to be separated into the organic solvent and dicyanobenzene by recovering the organic solvent together with methylbenzonitrile by-produced in the ammoxidation step (1) from the top of the column and taking out dicyanobenzene from the bottom of the column;
    (4) a hydrogenation step in which, after adding a reaction solvent, the separated dicyanobenzene from the distillation step is hydrogenated in a liquid phase in the presence of a Ni/diatomaceous earth catalyst to obtain a solution containing xylylenediamine; and
    (5) a purification step in which the solution containing xylylenediamine from the hydrogenation step is distilled to obtain a highly pure xylylenediamine,
    wherein:
    (i) said distillation step (3) is performed in a single distillation step in a single distillation column;
    (ii) the temperature of the column bottom in the distillation step (3) is 165 to 200° C.;
    (iii) the distillation column is operated under a pressure of 3 to 20 kPa during said distillation step (3); and
    (iv) at least a part of the organic solvent separated in the distillation step (3) is reused in the extraction step (2).

2. The method according to claim 1, wherein the reaction solvent used in the hydrogenation step contains liquid ammonia.

3. The method according to claim 1, wherein xylene is m-xylene and xylylenediamine is m-xylylenediamine.

4. The method according to claim 1, wherein a purity of xylylenediamine to be produced is 99.9% by weight or more.

* * * * *